United States Patent
Endo et al.

(10) Patent No.: US 7,070,924 B1
(45) Date of Patent: *Jul. 4, 2006

(54) METHOD OF DETECTING CELL DEATH AND DETECTION REAGENT

(75) Inventors: Fumio Endo, Kumamoto (JP); Naoto Adachi, Kumamoto (JP); Hiroyuki Nunoi, Miyazaki (JP); Keisuke Watanabe, Tsukuba (JP)

(73) Assignee: EISAI Co., Ltd., Tokyo (JP)

( * ) Notice: Subject to any disclaimer, the term of this patent is extended or adjusted under 35 U.S.C. 154(b) by 543 days.

This patent is subject to a terminal disclaimer.

(21) Appl. No.: 10/129,644

(22) PCT Filed: Nov. 8, 2000

(86) PCT No.: PCT/JP00/07838

§ 371 (c)(1),
(2), (4) Date: May 6, 2002

(87) PCT Pub. No.: WO01/35093

PCT Pub. Date: May 17, 2001

(30) Foreign Application Priority Data

Nov. 8, 1999 (JP) ............................... 11-316475
Sep. 11, 2000 (JP) ............................ 2000-274257

(51) Int. Cl.
*C12Q 1/26* (2006.01)
*C12Q 1/70* (2006.01)
*G01N 33/543* (2006.01)

(52) U.S. Cl. ............................. 435/5; 435/4; 435/7.21; 435/7.23; 435/7.24; 435/7.4; 435/7.94; 435/25; 436/518; 436/536; 436/86

(58) Field of Classification Search ..................... 435/4, 435/5, 7.21, 7.23, 7.24, 7.94, 25, 7.4; 436/518, 436/536, 86
See application file for complete search history.

(56) References Cited

U.S. PATENT DOCUMENTS

2002/0192712 A1* 12/2002 Endo et al. ................. 435/7.1
2004/0043435 A1*  3/2004 Los et al. ................. 435/7.23
2005/0106561 A1*  5/2005 Suzuki et al. ................. 435/5

FOREIGN PATENT DOCUMENTS

GB       2 241 782 A    9/1991
JP       03-257367      11/1991
WO       WO 98/02579    1/1998

OTHER PUBLICATIONS

Gvatua et al, Terapevticheskii Arkhiv, 62 (4), 58-61, 1990.*
Gvatua et al, Terapevticheskii Arkhiv, 62 (4), 58-61, 1990 (Abstract). Online, retrieved on Aug. 2, 2005 from STN International. Columbus, OH. Accession No. 1990:445440 BIOSIS.*
Hales et al, Methods in Enzymology, 70, 334-335, 1980.*
Fujimura, M., et al. "Cytosolic Redistribution of Cytochrome c After Transient Focal Cerebral Ischemia in Rats." *Journal of Cerebral Metabolism*, 18:1239-1247, 1998.
Antonawich, "Translocation of Cytochrome c Following Transient Global Ischemia in the Gerbil", *Neuroscience Letters*, 274: 123-126, 1999.
Dinsdale, et al., "Redistribution of Cytochrome c Precedes the Caspase-Dependent Formation of Ultracondensed Mitochondria, with a Reduced Inner Membrane Potential, in Apoptotic Monocytes", *American Journal of Pathology*, 155(2): 607-618, 1999.
Hetts, "To Die or Not to Die", *JAMA*, 279(4): 300-307, 1998.
Jemmerson, et al., "A Monoclonal Antibody Specific for a Cytochrome c T cell Stimulatory Peptide Inhibits T cell Responses and Affects the Way the Peptide Associates with Antigen-Presenting Cells", *European Journal of Immunology*, 21: 143-151, 1991.
Los, et al., "Cytochrome c is Rapidly Released from the Cell Upon Apoptosis Induction: A New Marker for Cell Death in vivo", *Immunology Letters*, 73(2-3): 239, 2000.
Shounan et al., "Apoptosis Detection by Annexin V Binding: A Novel Method for the Quantitation of Cell-Mediated Cytotoxicity", *Journal of Immunological Methods*, 217: 61-70, 1998.
Ushmorov, et al., "Nitric Oxide-Induced Apoptosis in Human Leukemic Lines Requires Mitochondrial Lipid Degradation and Cytochrome C Release", *Blood*, 93(7): 2342-2352, 1999.
Copy of European Search Report for related EP application No. 02253172.7.

* cited by examiner

*Primary Examiner*—David Saunders
(74) *Attorney, Agent, or Firm*—Brenda Herschbach Jarrell; Charles E. Lyon; Choate, Hall & Stewart, LLP

(57) ABSTRACT

A method for detecting cell death, which comprises determining cytochrome C in body fluid and detecting cell death based on a quantified value, as well as a method for determining cytochrome C in body fluid by a sandwich method and a reagent for measuring cytochrome C for determination cytochrome C in body fluid by a sandwich method, which comprises an antibody directed to cytochrome C as an ingredient.

7 Claims, 4 Drawing Sheets

METHOD OF DETECTING CELL DEATH AND DETECTION REAGENT

RELATED APPLICATIONS

This is the U.S. National Phase under 35 U.S.C. § 371 of International Application PCT/JP00/07838, filed Nov. 8, 2000, which claims the priority of Japanese Patent Application No. 11-316475, filed Nov. 8, 1999 and Japanese Patent Application No. 2000-274257, filed on Sep. 11, 2000.

TECHNICAL FIELD

The present invention relates to a method and a reagent for detecting cell death.

BACKGROUND ART

Graft versus host disease (GVHD), which is a disease that is caused after bone marrow transplantation and damages many organs; hemophagocytic syndrome (HPS), which is a disease where blood cells are phagocytized by phagocytes, especially virus associated hemophagocytic syndrome (VAHS) occurring after viral infection; and so forth are severe diseases that cause organ failures and eventually lead to death. Currently, cytologic diagnosis such as biopsy is generally used for diagnosing these diseases. However, such diagnosis suffers from drawbacks in view of patient's pain during the test, time required for diagnosis and operation procedures.

Since it has been found in recent years that a major cause of GVHD and HPS is cell apoptosis in living bodies, it is considered that GVHD and HPS may be diagnosed by detecting apoptosis.

As methods for detecting apoptosis, there have conventionally been used 1) morphologic methods, 2) histochemical methods, 3) biochemical methods and 4) immunochemical methods.

1) Morphologic Methods

There are used the chromatin codensation method, in which DNA fragmentation specifically occurring during apoptosis is detected by staining, and a method of detecting morphologic change specific to apoptosis by observation under an electron microscope or measurement of a cell size.

2) Histochemical Methods

There is used a method of ligating a labeled nucleotide to a terminus of a DNA fragment and detecting it by a fluorescence microscope. As another method, a flow cytometry is also used, in which amounts of intracellular substances are measured for individual cells.

3) Biochemical Methods

There is used a method of detecting a DNA ladder by agarose gel electrophoresis. This is currently considered to be the most reliable method for identifying apoptosis. However, since DNA is extracted from a tissue or a cell population as a whole, it is said that this method has a problem in sensitivity and quantitation performance when the proportion of apoptotic cells is not high.

4) Immunochemical Methods

A solid phase enzyme immunoassay (enzyme-linked immunosorbent assay, ELISA) for detecting histone-binding DNA fragments (mono- or oligo-nucleosome) has been developed (Cell Detection ELISA: Boehringer Mannheim, Kokusan Chemical).

However, these methods have problems such as complicated procedures and poor sensitivity and quantification performance, and have not been currently used in practice as methods for diagnosing GVHD and HPS.

DISCLOSURE OF THE INVENTION

An object of the present invention is to develop a method and a reagent for detecting apoptosis occurring in a living body, which are simple and show superior sensitivity and quantitation performance.

Cytochrome C is known as an important protein in the electron transport system in mitochondria. It is reported that, when a cell is exposed to a stimulus that triggers apoptosis and enters into an apoptosis state, cytochrome C in the mitochondria is rapidly released into cytosol (Dinsdale, D. et al., American J. Pathol. 155: 607–18, 1999). It is also reported that cytochrome C in the cytosol is associated with activation of caspase-3, which is a key factor of apoptosis, and an increase of cytochrome C is involved in the progress of apoptosis (Medina, V. et al., Cancer Research, 57: 3697–707, 1999).

The inventors of the present invention considered that, when apoptosis occurred in a living body, cytochrome C released from mitochondria could also be measured in blood. Then, they established an ELISA method for measuring cytochrome C, and found that the cytochrome C level in blood strongly correlated with progress of GVHD, HPS, acute lymphatic leukemia and influenzal encephalopathy. Thus, they accomplished the present invention.

The present invention provides a method for detecting cell death occurring in a living body by determining cytochrome C in body fluid, and a method and a reagent for measuring cytochrome C that can be used in such a method, which are described below.

(1) A method for detecting cell death, which comprises determining cytochrome C in body fluid and detecting cell death based on a determined value.

(2) The method for detecting cell death according to (1), wherein cytochrome C is determined by an immunochemical method.

(3) A method for measuring cytochrome c, which comprises determining cytochrome C in body fluid by a sandwich method.

(4) A reagent for measuring cytochrome C for determination of cytochrome C in body fluid by a sandwich method, which comprises an antibody directed to cytochrome C as an ingredient.

(5) The reagent for measuring cytochrome C according to (4), which is used for detection of cell death.

(6) The reagent for measuring cytochrome C according to (4), which is used for diagnosis of graft versus host disease (GVHD).

(7) The reagent for measuring cytochrome C according to (4), which is used for diagnosis of hemophagocytic syndrome (HPS).

(8) The reagent for measuring cytochrome C according to (4), which is used for diagnosis of acute lymphatic leukemia.

(9) The reagent for measuring cytochrome C according to (4), which is used for diagnosis of viral encephalitis or encephalopathy.

(10) The reagent for measuring cytochrome C according to (9), wherein the viral encephalitis or encephalopathy is influenzal encephalitis or encephalopathy.

BEST MODE FOR CARRYING OUT THE INVENTION

Figure 1:
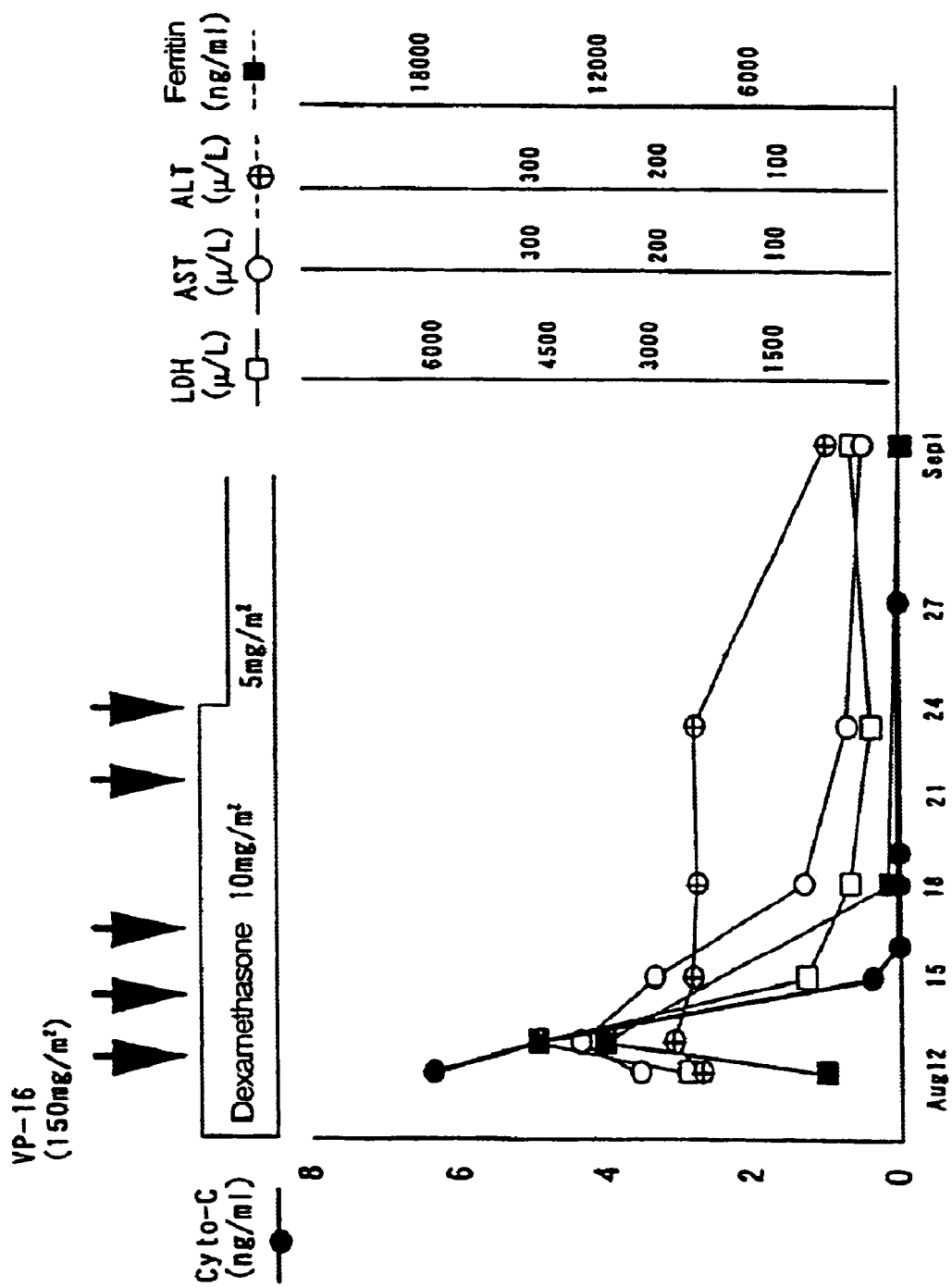
FIG. 1 shows changes in values of LDH, AST, ALT, ferritin and cytochrome C (Cyto-C) in sera of HPS patients.

Hereafter, embodiments of the present invention will be explained in detail.

It is considered that cytochrome C transferred from mitochondria to cytoplasm in response to an apoptosis signal is released outside a cell due to destruction of a cell membrane as a result of cell death. The present invention is based on findings that cytochrome C released outside a cell due to cell death can be detected by determining cytochrome C in body fluid such as blood, and that cell death occurring in a living body can be detected by determining cytochrome C in body fluid. Therefore, any methods for detecting cell death by determinining cytochrome C in body fluid fall within the scope of the present invention.

The term "cell death" used herein primarily refers to apoptosis. However, it is not easy to identify cell death generally occurring in a living body as apoptosis, and any cell death accompanied by an increase of cytochrome C in body fluid is included in the cell death referred to in the present invention.

Further, body fluid refers to blood, plasma, serum, cerebrospinal fluid or the like collected from a living body.

As the method for measuring cytochrome C, there can be mentioned an immunochemical method, method utilizing electrophoresis, method utilizing chromatography and so forth. Examples of the methods utilizing electrophoresis include a method wherein polyacrylamide gel electrophoresis is performed to detect cytochrome C as a band, a method wherein capillary electrophoresis is performed to detect cytochrome C as a peak and so forth. Further, as the method utilizing chromatography, a method wherein high performance liquid chromatography is performed to detect cytochrome C as a peak and so forth can be mentioned. In order to increase sensitivity, fluorescence labeling may be used in some cases, but the present invention is not limited to such cases.

As the method for measuring cytochrome C, an immunochemical method is preferred in view of sensitivity and simplicity. The term "immunochemical method" used herein refers to a method of determining cytochrome C by using an antibody directed to cytochrome C. As the immunochemical method, there can be mentioned various methods such as a competitive method in which cytochrome C is labeled, a sandwich method in which an antibody is labeled, a latex bead method in which agglutination of antibody-coated beads is observed and so forth, and they are included in preferred embodiments of the present invention so long as an antibody directed to cytochrome C is used. The antibody may be a monoclonal or polyclonal antibody. As the labeling method, there can also be mentioned various methods such as labeling with a radioactive isotope, labeling with a compound showing electro-chemiluminescence, fluorescence labeling, labeling with an enzyme, labeling with biotin and so forth, but the present invention is not limited to these examples.

As an example of the immunochemical method for measuring cytochrome C, a sandwich method will be explained below step by step.

1) An antibody directed to cytochrome C is immobilized on beads or a cup. The beads may be microbeads. In this case, microbeads of magnetic substance are preferred. The immobilization may be achieved by a covalent or non-covalent bond. Usually, nonspecific binding sites on the beads or cup are blocked by using a protein such as bovine serum albumin (BSA) or casein or a surfactant such as Tween 20.

2) A specimen is diluted with a buffer containing a protein such as BSA or casein or a surfactant such as Tween 20, if required, and added to the beads or the cup. Further, a known amount of cytochrome C is similarly diluted and added.

3) The beads or the cup are/is washed with a buffer containing a surfactant such as Tween 20, if required, and a labeled antibody diluted with a buffer containing a protein such as BSA or casein or a surfactant such as Tween 20, if required, is added thereto.

4) The beads or the cup are/is washed with a buffer containing a surfactant such as Tween 20, if required, and measurement is performed by a method corresponding with the label. For example, radioactivity is measured when it is radioactively labeled, or enzymatic activity is measured when it is labeled with an enzyme. Further, when it is labeled with biotin, labeled avidin is further added and measurement is performed by a method corresponding with the label.

5) A calibration curve is created by using known amounts of cytochrome C, and the amount of cytochrome C contained in the specimen is calculated.

With the above steps, cytochrome C in the specimen is determined.

When the determined value of cytochrome C is higher than a normal value, it can be considered that cell death is detected.

The present invention also relates to a method for measuring cytochrome C, which comprises determining cytochrome C in body fluid by a sandwich method. The sandwich method is an immunochemical method such as ELISA utilizing an antigen sandwiched by an immobilized antibody and a labeled antibody.

As the method for measuring cytochrome C by an immunochemical method, a dot blot method is widely used (Souichi A. et al., J. Biological Chem. 273: 19892–4, 1998). However, while this method can measure cytochrome C in a cell homogenate containing a high content of cytochrome C and a low concentration of protein, this is not suitable for determining cytochrome C with high sensitivity in body fluid containing a low content of cytochrome C and a high concentration of protein. The present invention is based on a finding that even such a trace amount of cytochrome C in body fluid as released due to cell death occurring in a living body can be detected by using ELISA based on the sandwich method to determine cytochrome C in the body fluid containing a high concentration of protein with high sensitivity.

Further, the present invention also relates to a reagent for measuring cytochrome C, which comprises an antibody directed to cytochrome C as an ingredient and used for determining cytochrome C in body fluid by the sandwich method. This measurement reagent may have the same constitution as that of a reagent (kit) used in a usual sandwich method except that the anti-cytochrome C antibody is used as an antibody. For example, the reagent for measuring cytochrome C by the sandwich method may contain 1) an anti-cytochrome C antibody-coated solid phase such as an anti-cytochrome C antibody-coated cup or anti-cytochrome C antibody-coated beads, 2) a labeled anti-cytochrome C antibody, 3) a cytochrome C standard solution of a known concentration, 4) a diluent and 5) a washing solution. Further, if labeling with an enzyme is used, 6) a chromogenic substrate and 7) a solution for terminating a reaction may be included.

The method and the reagent for measuring cytochrome C disclosed by the present invention enable detection of cell death. Therefore, it becomes possible to provide a diagnostic indicator for diagnosis of various diseases accompanied with apoptosis such as differential diagnosis or follow-up of the diseases. Thus, there are provided a method and reagent for measuring cytochrome C for the purpose of detection of cell death or diagnosis of a disease accompanied with apoptosis.

As examples of the diseases accompanied with apoptosis, the followings can be mentioned.

1) Diseases in which apoptosis is induced in response to a signal generated by a cell of an immune system responsible for biophylaxis, for example, GVHD and autoimmune diseases (systemic lupus erythematosus (SLE), rheumatoid arthritis (RA), scleroderma, Sjogren's syndrome, multiple sclerosis, insulin dependent diabetes mellitus, ulcerative colitis)

2) Diseases in which cell death is induced by viral infection or apoptosis is induced by reaction of a cell of an immune system with a cell infected by a virus, for example, virus associated hemophagocytic syndrome (VAHS) and other viral infections (HCV, HIV, influenza virus)

3) Diseases in which cell death is induced by an abnormal apoptosis signal, for example, neurodegenerative diseases (Alzheimer's disease, Parkinson's disease)

4) Leukemia, for example, acute lymphatic leukemia

5) Diseases in which apoptosis is artificially induced by, for example, radiation exposure or medication (anticancer drug etc.)

6) Systemic inflammatory reaction syndrome (SIRS), diseases in which organ disorder occurs because the immune system is nonspecifically activated in response to invasion to a living body and thus control of cytokine production becomes impossible (HPS, severe pancreatitis)

Among the diseases induced by viral infection, those that are severe and likely to leave aftereffects are encephalitis and encephalopathy. In particular, encephalitis and encephalopathy caused by influenza virus account for a large proportion of causes of death by influenza, but it is difficult to differentiate the diseases from heat cramp, and a method of accurate early diagnosis for providing appropriate treatment therefor is required. The measurement method and the measurement reagent of the present invention enable accurate and early diagnosis.

By measuring cytochrome C in body fluid, cell death progressing in a living body can be determined, and hence progress of these diseases can be monitored. In particular, in GVHD, hemophagocytic syndrome (HPS), especially virus associated hemophagocytic syndrome (VAHS), acute lymphatic leukemia and influenzal encephalitis or encephalopathy, determination of cytochrome C is useful to understand the conditions of the diseases.

As a result of further studies of the inventors of the present invention, it was confirmed that the cytochrome C level in blood well correlated with LDH, which was regarded as an indicator of cell death, in HPS and influenzal encephalopathy, and it was further revealed that increase and decrease of cytochrome C preceded those of LDH.

Cytochrome C in body fluid is a favorable indicator of cell death occurring in a living body, and can be a useful indicator to find a pathological condition early and accurately.

EXAMPLES

The present invention will be explained more specifically with reference to the following examples. However, the scope of the present invention is not limited to these examples. % refers to % by mass unless otherwise indicated.

Example 1

Measurement of Cytochrome C by ELISA

Cytochrome C is measured by the following procedure.

1) Purification of Anti-Cytochrome C Antibody

A rabbit is immunized with rat cytochrome C (Sigma) to obtain antiserum directed to cytochrome C. To the antiserum, ammonium sulfate is added at a final concentration of 2 M, and it is stirred at room temperature (20–30° C.) for 5 hours. The stirred solution is centrifuged at 10000 rpm for 30 minutes and the supernatant is discarded. The precipitation is dissolved in 0.1 M phosphate buffer (pH 7.2) and dialyzed against the same buffer. The dialyzed solution is applied to a column of a carrier obtained by binding bovine cytochrome C to CNBr-Sepharose 4B (Pharmacia). The column is washed with 0.01 M Tris-HCl buffer (pH 7.5) containing 0.15 M NaCl, and then anti-cytochrome C antibodies are eluted with 0.1 M guanidine hydrochloride. The eluted solution is dialyzed against 0.01 M Tris-HCl buffer (pH 7.5) containing 0.15 M NaCl to obtain purified antibodies (IgG).

2) Preparation of Anti-Cytochrome C Antibody F(ab')$_2$

The purified IgG is dialyzed against 0.1 M acetate buffer (pH 4.2). To the dialyzed IgG solution, pepsin (Sigma) is added in a mass concentration ratio of 20:1 and it is allowed to react at 37° C. for 16 hours. The solution after the reaction is adjusted to pH 7.5 with 1 N NaOH and subjected to gel filtration by using a Sephacryl S-200 (Pharmacia) column equilibrated with 0.01 M Tris-HCl buffer (pH 7.5) containing 0.15 M NaCl. A first peak of the fractions obtained from the gel filtration is collected and concentrated to obtain an anti-cytochrome C antibody F(ab')$_2$ solution.

3) Preparation of Horseradish Peroxidase (HRP)-Labeled Anti-Cytochrome C Antibody F(ab')$_2$ To 1 ml of HRP (Toyobo) solution adjusted to 4 mg/ml, 60 μl of 0.1 M sodium metaperiodate is added, and it is stirred at room temperature (20–30° C.) for 20 minutes, and dialyzed against 0.001 M acetate buffer (pH 4.4). The dialyzed solution is adjusted to pH 9.0–9.5 with 0.2 M sodium carbonate solution. To this solution, 1 ml of the anti-cytochrome C antibody F(ab')$_2$ solution (4 mg/ml) dialyzed against 0.1 M carbonate buffer (pH 9.5) is added and it is stirred at room temperature (20–30° C.) for 2 hours. Then 50 µl of sodium borohydride solution adjusted to 4 mg/ml is added, and it is stirred at 4° C. for 2 hours and left standing for 16 hours. This solution is dialyzed against a phosphate buffer (pH 7.2) containing 0.15 M NaCl and then subjected to gel filtration by using a Sephacryl S-200 (Pharmacia) column. A first peak of the fractions obtained from the gel filtration is collected and diluted with 0.2 M disodium phosphate buffer (pH 5.4) containing 25% rabbit serum (Nippon Seibutsu Zairyo) to obtain a HRP-labeled anti-cytochrome C antibody F(ab')$_2$ solution (labeled antibody solution).

4) Preparation of Anti-Cytochrome C Antibody-Immobilized Cup

The purified IgG obtained in 1) is adjusted to an absorbance of 0.1 with 0.01 M Tris-HCl buffer (pH 7.5). 100 µl of this antibody solution is introduced into a polystyrene cup, and allowed to react at 4° C. for 16 hours and the cup is washed three times (for 4 seconds each time) with 0.01 M Tris-HCl buffer (pH 7.5) containing 0.15 M NaCl and 0.01% Tween 20 by using a washer designed for use in EIA. 200 µl of 0.01 M Tris-HCl buffer (pH 7.5) containing 0.5% bovine albumin is added to the washed cup and allowed to react at 4° C. for 16 hours again to obtain an antibody-immobilized solid phase cup.

5) Preparation of Standard Antigen

Rat cytochrome C (Sigma) is diluted with 0.05 M Tris buffer (pH 7.5) containing 2% BSA, 0.01 M EDTA 2Na, 0.1% NaN$_3$, 0.01% Tween 20 and 0.15 M NaCl to prepare 50-0.05 ng/ml dilutions.

6) Measurement

The bovine albumin solution in the anti-cytochrome C antibody-immobilized cup is sucked out and 50 µl of 0.05 M Tris buffer (pH 7.5) containing 2% BSA, 0.01 M EDTA 2Na, 0.1% NaN$_3$, 0.01% Tween 20 and 0.15 M NaCl is introduced into the aforementioned cup. 50 µl each of diluted standard antigen solutions and a specimen is added to the cup and allowed to react at room temperature (20–30° C.) for 1 hour. After the reaction, the cup is washed three times (for 4 seconds each time) with 0.005 M Tris buffer (pH 7.5) containing 0.01% Tween 20, 0.0015 M NaCl, 0.0015% methyl paraoxybenzoate and 0.005% 2-chloroacetamide by using a washer designed for use in EIA. After the washing, 100 µl of the labeled antibody solution is added and allowed to react at room temperature (20–30° C.) for 1 hour. After the reaction, the cup is washed three times (for 4 seconds each time) with 0.005 M Tris buffer (pH 7.5) containing 0.01% Tween 20, 0.15 M NaCl, 0.0015% methyl paraoxybenzoate and 0.005% 2-chloroacetamide by using a washer designed for use in EIA. After the washing, 100 µl of 0.1 M citrate buffer (pH 4.2) containing 1.5 mg/ml ABTS (2,2-azino-bis-(3-ethylbenzothiazoline-6-sulfonic acid) is added and allowed to react at room temperature (20–30° C.) for 1 hour, and then 100 µl of 0.013% NaN$_3$ solution is added to terminate the reaction. The absorbance of the color-developed solution is measured at 405 nm by using a spectrophotometer.

7) Characteristics of Standard Antigen Curve

Absorbance value of a blank is subtracted from each of absorbance values of the cytochrome C at various concentrations and the specimen. The standard antigen concentration and the absorbance of the standard antigen are plotted on the horizontal axis and the vertical axis, respectively, to draw a standard curve. Based on the standard antigen curve, the amount of cytochrome C contained in the specimen is calculated.

Example 2

Quantitation of Cytochrome C in Sera of GVHD, HPS and Acute Lymphatic Leukemia Patients Cytochrome C levels in sera of GVHD, HPS and acute lymphatic leukemia patients and normal subjects were measured by using the ELISA system for measuring cytochrome C described in Example 1.

As a result, as shown in Table 1, 15 normal subjects were all negative (<0.05 ng/ml), whereas 4 out of 6 GVHD patients were positive (67%), 4 out of 4 HPS patients were positive (100%) and 2 out of 2 acute lymphatic leukemia patients were positive (100%). Further, HPS patients having a high blood cytochrome C concentration tended to show poor course of the disease.

Clearly high determined values of cytochrome C were observed in sera of patients where apoptosis was considered to occur.

TABLE 1

Determined values of cytochrome C in sera of GVHD, HPS and acute lymphatic leukemia patients

| Disease | Determined value of cytochrome C in serum (ng/ml) |
|---|---|
| GVHD | 1.1 |
|  | <0.05 |
|  | 0.4 |
|  | 0.3 |
|  | <0.05 |
|  | 0.3 |
| HPS (including VAHS) | 3.1 |
|  | 22.0 |
|  | 38.0 |
|  | 2.9 |
| Acute lymphatic leukemia | 0.4 |
|  | 0.4 |
| Normal subjects* | <0.05 |

*All the 15 normal subjects had values less than the detection limit (<0.05 ng/ml).

Further, changes in values of LDH, AST, ALT, ferritin and cytochrome C in sera of HPS patients are shown in FIG. 1. The cytochrome C value substantially correlated with the LDH and its change preceded that of LDH. Therefore, cytochrome C is considered to be useful as an indicator for sensitively reflecting changes in pathological conditions.

Example 3

Determination of Cytochrome C in Sera of Influenzal Encephalitis or Encephalopathy Patients The amounts of cytochrome C in sera of influenza patients accompanied with high fever, heat cramp or encephalitis or encephalopathy were measured by using the ELISA system described in Example 1.

Figure 2:
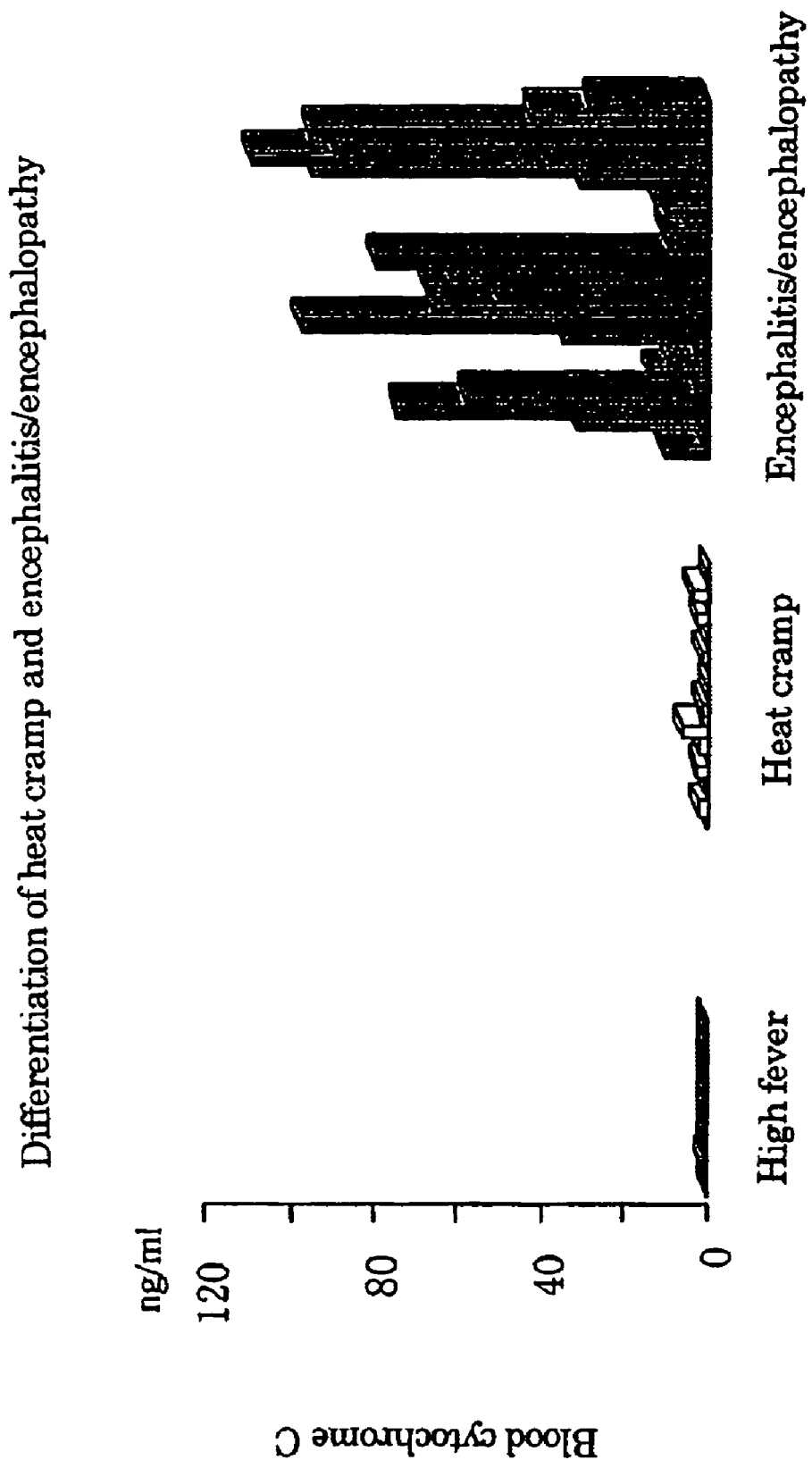
FIG. 2 shows cytochrome C levels in sera of influenza patients accompanied with high fever, heat cramp or encephalitis or encephalopathy.

The results including those of multiple measurements for one patient are shown in FIG. 2. Among the cases accompanied with encephalitis or encephalopathy, all 27 specimens (8 cases) showed high values not lower than 5 ng/ml, and among these, 17 specimens showed high values not lower than 30 ng/ml. Further, patients having a high blood cytochrome C concentration tended to show poor course of the disease.

Some patients having repeated heat cramps showed slightly high values, and it was considered that a sufficient care was necessary for these patients. Among patients accompanied with high fever, no patient showed a high determined value of cytochrome C.

Figure 3:
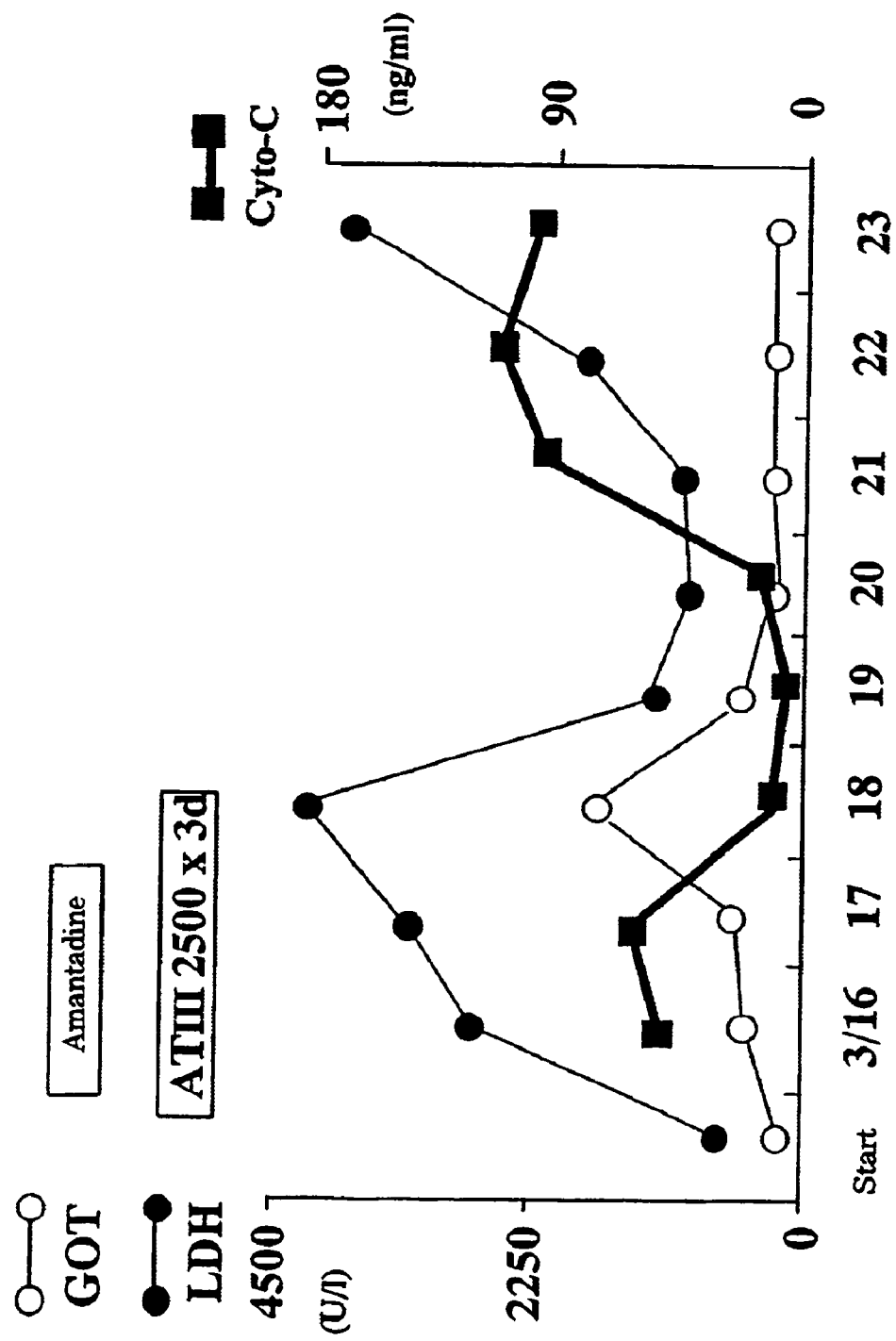
FIG. 3 shows changes in values of GOT, LDH and cytochrome C in blood of patients having developed influenzal encephalopathy.

Further, changes in values of GOT, LDH and cytochrome C in blood of influenzal encephalopathy patients are shown in FIG. 3. Increase and decrease of the cytochrome C level preceded those of LDH, and it was revealed that cytochrome C was useful as a preceding indicator reflecting a pathological condition of influenzal encephalopathy.

Example 4

Concentrations of Various Cytokines in Sera of Influenzal Encephalitis or Encephalopathy Patients Concentrations of E-selectin, soluble thrombomodulin (sTM), tumor necrosis factor (TNF), Fas, FasL and cytochrome C in sera of influenza patients accompanied with high fever, heat cramp or encephalitis or encephalopathy were determined. E-selectin was measured by using sE-Selectin ELISA Kit (Version 2, Bender Med Systems). sTM was measured by using TM Test (Teijin Diagnostics). TNF was measured by using Human TNF-α Cytoscreen Immunoassay Kit (Biosource International). Fas was measured by using sFas ELISA Kit, and FasL was measured by using sFas Ligand ELISA Kit (both produced by Medical and Biological Laboratories). Cytochrome C was measured by using the ELISA system described in Example 1.

Figure 4:
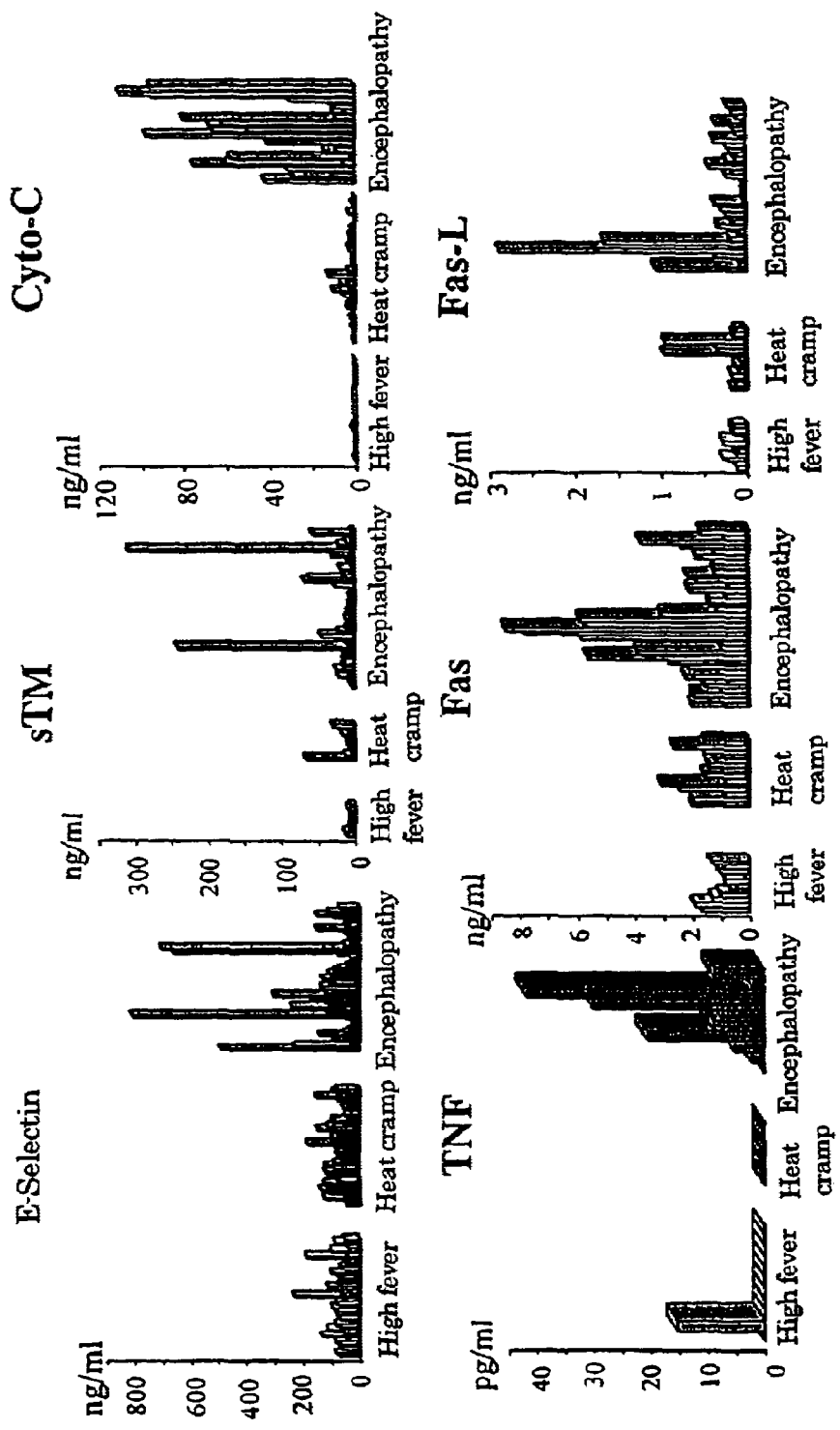
FIG. 4 shows levels of various cytokines in sera of influenza patients accompanied with high fever, heat cramp or encephalitis or encephalopathy.

As shown in FIG. 4, for all of the cytokines, number of cases showing high determined values increased for sera of encephalitis or encephalopathy patients. However, cytochrome C most markedly increased in encephalitis or encephalopathy patients. Thus, it was revealed that cytochrome C was the most suitable for differential diagnosis of encephalitis or encephalopathy.

INDUSTRIAL APPLICABILITY

The present invention provides an immunochemical method suitable for determination of cytochrome C in body fluid. Further, it was revealed that cytochrome C was a favorable indicator of cell death occurring in a living body and a useful indicator to find a pathological condition early and accurately. Therefore, measurement of cytochrome C is useful for diagnosis such as differential diagnosis or follow-up of diseases in which apoptosis is involved in progress of their pathological conditions, in particular, GVHD, HPS, acute lymphatic leukemia and influenzal encephalitis or encephalopathy.

What is claimed is:

1. A method for detecting apoptosis, which comprises:
   measuring a level of cytochrome C in a body fluid and
   detecting apoptosis based on the level of cytochrome C measured in the measuring step.

2. The method according to claim 1, wherein the level of cytochrome C is measured by an immunochemical method.

3. A method for diagnosing graft versus host disease, which comprises:
   measuring a level of cytochrome C in a body fluid, and
   diagnosing graft versus host disease based on the level of cytochrome C measured in the measuring step.

4. A method for diagnosing hemophagocytic syndrome, which comprises:
   measuring a level of cytochrome C in a body fluid, and
   diagnosing hemophagocytic syndrome based on the level of cytochrome C measured in the measuring step.

5. A method for diagnosing acute lymphatic leukemia, which comprises:
   measuring a level of cytochrome C in a body fluid, and
   diagnosing acute lymphatic leukemia based on the level of cytochrome C measured in the measuring step.

6. A method for diagnosing viral encephalitis or encephalopathy, which comprises:
   measuring a level of cytochrome C in a body fluid, and
   diagnosing viral encephalitis or encephalopathy based on the level of cytochrome C measured in the measuring step.

7. The method according to claim 6, wherein the viral encephalitis or encephalopathy is influenzal encephalitis or encephalopathy.

\* \* \* \* \*